US009573905B2

(12) United States Patent
Contreras et al.

(10) Patent No.: US 9,573,905 B2
(45) Date of Patent: Feb. 21, 2017

(54) PROCESS TO OBTAIN MIXTURES OF IMIDAZOLINES AND CORROSION INHIBITORS FROM COFFEE WASTE

(71) Applicants: CORROSION Y PROTECCION SA DE CV, Cuernavaca Morelos (MX); UNIVERSIDAD NACIONAL AUTONOMA DE MEXICO, Coyoacan, Mexico City (MX)

(72) Inventors: Jose Ignacio Regla Contreras, Benito Juarez (MX); Maria Patricia Shirley Demare Negrete, Mexico City (MX); Jorge Antonio Ascencio Gutierrez, Cuernavaca Morelos (MX); Lorenzo Martinez Gomez, Cuernavaca Morelos (MX); Lorenzo Martinez Martinez De La Escalera, Mexico City (MX); Jorge Joaquin Canto Ibanez, Mexico City (MX); Irene Carrillo Salgado, Boca del rio Veracruz (MX)

(73) Assignees: CORROSION Y PROTECCION SE DE CV, Cuernavaca Morelos (MX); UNIVERSIDAD NACIONAL AUTONOMA DE MEXICO, Coyoacan, Mexico City (MX)

(*) Notice: Subject to any disclaimer, the term of this patent is extended or adjusted under 35 U.S.C. 154(b) by 0 days.

(21) Appl. No.: 14/220,596

(22) Filed: Mar. 20, 2014

(65) Prior Publication Data
US 2015/0225351 A1 Aug. 13, 2015

(30) Foreign Application Priority Data
Feb. 13, 2014 (MX) .................. MX/A/2014/002086

(51) Int. Cl.
*C07D 233/06* (2006.01)
*C07D 233/14* (2006.01)
*C23F 11/14* (2006.01)
*C05F 5/00* (2006.01)

(52) U.S. Cl.
CPC ............ *C07D 233/06* (2013.01); *C05F 5/006* (2013.01); *C07D 233/14* (2013.01); *C23F 11/149* (2013.01); *Y02E 50/343* (2013.01); *Y02W 30/47* (2015.05)

(58) Field of Classification Search
None
See application file for complete search history.

(56) References Cited

U.S. PATENT DOCUMENTS

| | | |
|---|---|---|
| 2,161,938 A | 6/1939 | Sonn |
| 2,200,815 A | 5/1940 | Radcliffe |
| 5,049,315 A | 9/1991 | Hitz et al. |
| 5,154,841 A | 10/1992 | Tucker et al. |
| 6,448,411 B1 | 9/2002 | Meyer |
| 6,488,732 B2 | 12/2002 | Scanlan |
| 8,540,881 B1 | 9/2013 | Shah et al. |
| 8,545,702 B1 | 10/2013 | Shah et al. |
| 2007/0259084 A1 | 11/2007 | Gaonkar et al. |
| 2010/0287823 A1 | 11/2010 | Misra et al. |

FOREIGN PATENT DOCUMENTS

| | | |
|---|---|---|
| AR | 075138 | 3/2011 |
| CN | 102875160 | 1/2013 |
| JP | 2013013344 | 1/2013 |

OTHER PUBLICATIONS

Daglia et al. Journal of Agricultural and Food Chemistry 2004, vol. 52, p. 1700-1704, "In Vitro and ex Vivo Antihydroxyl Radical Activity of Green and Roasted Coffee."
Rivera-Grau et al. Int. J. Electrochem. Sci. 2012, vol. 7, p. 12391-12403, "H2S Corrosion Inhibition of Carbon Steel by a Coconut-Modified Imidazoline."
Williams et al. Journal of Environmental Quality, Technical Reports, Organic Compounds in the Environment Sep.-Oct. 2012, vol. 41, No. 5, p. 1473-1480, "Soil Persistence and Fate of Carbamazepine, Lincomycin, Caffeine, and Ibuprofen from Wastewater Reuse."
Al-Hamamre et al. Fuel 2012, vol. 96, p. 70-76, "Oil extracted from spent coffee grounds as a renewable source for fatty acid methyl ester manufacturing."
Barkenbus et al. Journal of American Chemical Society 1927, vol. 49, p. 2061-2064, "Kentucky Coffee Nut Tree Seed Oil".
Couto et al. J. of Supercrotocal Fluids 2009, vol. 51, p. 159-166, "Supercritical fluid extraction of lipids from spent coffee grounds."
Kondamudi et al. J. Agric. Food Chem. 2008, vol. 56, p. 11757-11760, "Spent Coffee Grounds as a Versatile Source of Green Energy."
Martin et al. Talanta 2001, vol. 54, p. 291-297, "Fatty acid profiles as discriminant parameters for coffee varieties differentiation."
Oliveira et al. Bioresource Technology 2008, vol. 99, p. 3244-3250, "Coffee oil as a potential feedstock for biodiesel production."

(Continued)

*Primary Examiner* — Samantha Shterengarts
(74) *Attorney, Agent, or Firm* — Brooks Kushman P.C.

(57) ABSTRACT

The biphasic extraction from coffee waste without a prior drying process, to obtain coffee oil, which is transesterified with KOH catalyzed methanol to produce mixtures of glycerol free methylic esters, also known as coffee oil biodiesel, which is subjected to an aminolysis reaction with aminoethylethanolamine (AEEA) by heating to 140-160° C. at atmospheric pressure with a subsequent dehydration reaction at the same temperature but at a reduced pressure of 200 to 300 mmHg, in order to achieve cyclization of the intermediary amides into the corresponding imidazolines. Alternatively process, coffee oil can be submitted to the same aminolysis procedure with aminoethylethanolamine (AEEA) at 140 to 160° C. and atmospheric pressure with a subsequent dehydration reaction at the same temperature but at a reduced pressure of 200 to 300 mmHg, to produce imidazolines that contain the residual glycerol of the original triglycerides.

2 Claims, 6 Drawing Sheets

(56) References Cited

OTHER PUBLICATIONS

Ortega-Toledo et al. Corrsion Science 2011, vol. 53, p. 3780-3787, "Co2 corrosion inhibition of X-120 pipeline steel by a modified imidazoline under flow conditions."

Yoo et al. Corrsion Science 2012, vol. 59, p. 42-54, "Synthesis and corrosion inhibition behavior of imidazoline derivatives based on vegetable oil."

Quandt et al. ACS Synth. Biol. 2013, vol. 2, p. 301-307, "Decaffeination and Measurement of Caffeine Content by Addicted *Escherichia coli* with a Refactored N-Demethylation Operon from Pseudomonas putida CBB5."

Abdullah et al. Reneqable Energy 2013, vol. 50, p. 965-970, "Oil removal from waste coffee grounds using two-phase solvent extraction enhanced with ultrasonication."

Khan et al. The Journal of the American Oil Chemists' Society Dec. 1953, vol. 30, Issue 12, p. 606-609, "The Composition of Coffee Oil and Its Component Fatty Acids."

Test of the 2-alkyl-1-hydroxiethyl imidazolines as a corrosion inhibitor at a concentration of 5 ppm.

FIGURE 4A

Test of the 2-alkyl-1-hydroxiethyl imidazolines as a corrosion inhibitor at a concentration of 10 ppm.

FIGURE 4B

Test of the 2-alkyl-1-hydroxiethyl imidazolines as a corrosion inhibitor at a concentration of 25 ppm.

FIGURE 4C

Test of the 2-alkyl-1-hydroxiethyl imidazolines as a corrosion inhibitor at a concentration of 50 ppm.

FIGURE 4D

Test of the 2-alkyl-1-hydroxiethyl imidazolines as a corrosion inhibitor at a concentration of 100 ppm.

FIGURE 4E

PROCESS TO OBTAIN MIXTURES OF IMIDAZOLINES AND CORROSION INHIBITORS FROM COFFEE WASTE

CROSS-REFERENCE TO RELATED APPLICATIONS

This application claims priority to Mexican Patent Application No. MX/a/2014/002086, filed Feb. 13, 2014, the disclosure of which is incorporated in its entirety by reference herein.

TECHNICAL FIELD

This invention includes innovating processes related to the extraction and processing of oils contained in coffee waste, including their transformation into substituted 1-hydroxyethyl-2-alkyl-imidazolines and their application as corrosion inhibitors on pipelines, containers and other industrial facilities for transport, storage and processing of liquid and gas hydrocarbons. The incorporation in the molecular structure of the doubly unsaturated linoleic acid contained in coffee oil triglycerides confers to these imidazolines a superior adherence to metallic surfaces, due to the interaction of the pi electrons of the double bonds with the electrons of the metallic surface. This invention also represents a solution to decontaminate coffee waste, which is recognized as a soil and water bank pollutant due to the toxic nature of caffeine, through a process where residual caffeine is eliminated from coffee waste.

BACKGROUND

Interior corrosion in pipelines, containers and processing facilities is a serious issue that jeopardizes a safe, reliable and environmentally harmless operation of industrial processes. Most metallic materials are very vulnerable to contact with water and a variety of electrolytes. This is a particularly serious problem in the oil industry, due to the growing total salinity and acidity of primary production, which has an impact in the entire chain of transport, refining and distribution processes.

Interior corrosion in pipelines, containers and industrial facilities caused by transport, storage or processing of fluids that contain water and electrolytes can be controlled using corrosion inhibitors.

The process of adding corrosion inhibitors to hydrocarbons being transported, stored or processed has proven significantly successful in mitigating corrosion to levels below two thousands of an inch per year, a parameter that is a requirement for many regulations to ensure several decades of useful life for metallic components (Norm NRF-005-PEMEX-2009). There's a wide variety of products that serve as corrosion inhibitors, one of the most important ones is the family of compounds known as imidazolines, which inhibit corrosion in low dosages from 5 to 150 ppm, and are considered amongst the most environmental friendly substances used in the industry. 2-Alkyl-imidazolines have been used as corrosion inhibitors in the oil industry since the 1940's. These inhibitors are used as mixtures of imidazolines with a hydrocarbonated chain of 7 to 19 carbon atoms (hydrophobic group) in position two, and a polar group in position one, such as hydroxyethyl or acylaminoethyl. Imidazolines can also be quaternized to be employed as cationic surfactants, fabric softeners, hair conditioners or antistatics.

Imidazolines of the 2-(2-alkyl-4,5-dihydro-1H-imidazol-1-il)ethanol type, extracted from vegetable oils such as palm or coconut oil, or animal fats, are commercially traded for different applications. An important usage for this type of compounds is corrosion inhibition for pipelines, containers and other facilities, property of industries that transport, process and store hydrocarbons. However, obtaining or applying imidazolines derived from oils extracted from coffee waste has never been conceived before. Even when coffee oil is well-known as a source of biofuels, no other process has been reported to obtain imidazolines derived from coffee oil. Coffee waste resulting from residue left over from the preparation of coffee beverages and other coffee based products, contain between 13 and 15% (dry base) of oil, which includes linoleic acid as the most abundant fatty acid found in this oil. Linoleic acid is doubly unsaturated, conferring the imidazolines containing it a superior adherence to metallic surfaces, due to the interaction of the pi electrons of the double bonds with the electrons of the metallic surface.

Imidazolines derived from coffee oil show, besides excellent qualities as corrosion inhibitors, low toxicity and good biodegradability, which makes them a very appropriate and environmentally friendly option as corrosion inhibitors for the industry as well as being suitable for applications such as fabric softeners, antistatic agents, hair conditioners, etc.

Coffee is one of the most important agricultural products worldwide and is also one of the most popular beverages with a very high level of consumption. It is estimated that worldwide, coffee production is close to 6 million tons, with ten leading countries. Coffee consumption is varied, from 12 Kg per capita in Finland, to a general average of 1.2 kg per capita. Depending on variety, the content of oil in coffee waste fluctuates between 13-18% (dry base). Most of ground coffee bean residue is disposed of in landfills, even though it has been proposed to use it to produce compost. Coffee waste is known as a soil and water bank pollutant, due to the toxic properties of caffeine.

Coffee oil is a mixture of triglycerides constituted by fatty acids of 14 to 22 carbon atoms, with a composition of fatty acids that depends on the type and origin of the coffee. It has been reported a composition of 44% linoleic acid, 33% palmitic acid, 9% oleic acid, 7% stearic acid and other fatty acids in minor contents.

Several processes have been described for coffee oil extraction, as a starting material for biodiesel. These processes employ soxhlet equipment, supercritical $CO_2$ for dry coffee waste, as well as ultrasound assisted biphasic extraction.

The procedures mentioned above for extraction of oil from coffee are, from our point of view, not feasible on an industrial scale, given that they require coffee that has been previously dried, as well as very costly industrial equipment, such as those that would demand the use of ultrasound or supercritical $CO_2$.

Specialized literature shows relevant references on the history and scientific breakthroughs that support this invention: Ortega-Toledo, D. M.; Gonzalez-Rodriguez, J. G.; Casales, M.; Martinez-Gomez, L. Corrosion Science, 53, 3780-3787 (2011); Radcriffe, R. U.S. Pat. No. 2,200,815 (1940); Meyer, G. R., U.S. Pat. No. 6,448,411 (2002); Daglia, M; Racchi, M.; Papetti, A.; Lanni, C.; Govoni, S.; Gazzani, G. Journal of Agricultural and Food Chemistry, 52, 1700-1704 (2004); Barkenbus, C.; Zimmerman, A. J. Journal of the American Chemical Society 49, 2061-2064 (1927); Kondamudi, N.; Mohapatra, S. K.; Misra, M. Journal of Agricultural and Food Chemistry 56 (24), 11757-11760 (2008); Scanlan, J. U.S. Pat. No. 6,488,732 (2002); Martin, M. J. et al., Talanta, 54, 291-297 (2001); Misra, M.;

Mohapatra, S. K.; Kondamudi, N. V. US 2010/0287823; Couto, R. M.; Fernandes, J.; Gomes da Silva, M. D. R.; Simoes, P. C. J. Supercritical Fluids, 51(2), 159-166 (2009); Oliveira, L. S.; Franca, A. S.; Camargos, and Ferraz, V. P. Bioresource Technology 99, 3244-3250 (2008); Abdullah, M.; Bulent Koc, A. Renewable Energy 50, 965-970 (2013); Al-Hamamre, Z.; Foerster, S.; Hartmann, F.; Kroger, M.; Kaltschmitt, M. Fuel, 96, 70-76 (2012); Khan, N. A.; Brown, J. B. Journal of the American Oil Chemists' Society, 30, 606-609 (1953); Seung-H. Yoo, Young-Wun Kim, Kunwoo Chung, Seung-Yeop Baik, Joon-Seop Kim. Corrosion Science, 59, 42-54 (2012); Rivera-Grau, L. M.; Casales, M.; Regla I.; Ortega-Toledo, D. M.; Ascencio-Gutierrez, J. A.; Gonzalez-Rodriguez, J. G.; Martinez-Gomez, L. International Journal of Electrochemical Science, 7, 12391-12403 (2012); Erik M. Quandt, Michael J. Hammerling, Ryan M. Summers, Peter B. Otoupal, Ben Slater, Razan N. Alnahhas, Aurko Dasgupta, James L. Bachman, Mani V. Subramanian, and Jeffrey E. Barrick, ACS Synth. Biol., Mar. 8, 2013; Williams C F, McLain J E, J Environ Qual. 2012 September-October; 41(5): 1473-80.

Amongst the patents reviewed to sustain the originality of the invention, patent JP2013013344 introduces a method for production of coffee oil for aromatic applications, where oil is extracted from roasted coffee beans hydrated with an oil/water emulsion using a centrifuge. This patent does not mention using the linoleic acid contained in the triglycerides present in the oil that has been extracted from coffee to obtain imidazolines, whose main quality is high adherence to metallic structures.

The patent with registration number CN 102875160 A introduces an invention related to the production of ceramic compound based additives using microwave radiation induction processes, hydroxymethylation and esterification where the raw materials are the lignosulphonates extracted from ground coffee. This patent does not describe any process related to the production of coffee biodiesel and imidazolines, such as the process of transesterification with KOH catalyzed methanol and aminolysis with aminoethylethanolamine (AEEA) respectively.

The patent with registration number US2007/0259084 A1 is related to the extraction of coffee surfactants using sugar transesterification and coffee oil, whose porpoise is the production of emulsions of this organic compound to improve coffee products, such as instant coffee, improving its aroma and taste. Likewise, this patent does not contemplate the use of coffee oil nor the processes inherent to extracting imidazolines for their use as corrosion inhibitors in the hydrocarbon industry.

The patent with registration number AR2010P100096 20100115 introduces a method to obtain biodiesel from coffee grounds. The purpose of this invention is to recycle coffee residue to produce a renewable fuel, with low environmental impact, however it makes no reference about any method or process to use organic coffee residue to inhibit interior corrosion in pipelines, containers and other industrial facilities related to storage and transport of hydrocarbons.

The patent with registration number US 2010/0287823 A1 describes a method for the production of a biofuel using one or more sources of coffee as raw material, such as green coffee grains, roasted coffee grains, ground coffee or ground coffee byproducts. This biofuel is extracted using a transesterification procedure of the triglycerides found in the coffee sources mentioned above, where the products obtained can be used for other purposes such as the production of cosmetics, drugs, food or fuel materials, however this patent does not consider an aminoethylethanolamine aminolysis (AEEA) process for the production of imidazoline mixtures.

Other patents reviewed, contemplate the production of biofuels, patents U.S. Pat. No. 8,545,702 y U.S. Pat. No. 8,540,881 B1, which are related to the production of biodiesel and/or glycerin from various processes, such as oil transesterification. These patents do not consider the use of coffee residue, nor the extraction of its oil as raw material for the production of corrosion inhibitors.

Likewise, there are patents related to obtaining imidazolines and their byproducts from chemical processes for various applications, such as processing of imidazolines of polycarboxylic acids for production of cleaning products (U.S. Pat. No. 5,049,315) imidazolines (U.S. Pat. No. 2,161,938), process for the preparation of substituted imidazoline as a fabric softener for the textile industry (U.S. Pat. No. 5,154,841). However, none of these patents make reference to the processing of coffee residue and using the linoleic acid contained in the triglycerides of the oil extracted from coffee for the synthesis of 2-alkyl-1-hidroxiethyl imidazolines which is doubly unsaturated and its main feature is high adherence to metallic surfaces.

SUMMARY

The main novelty provided by this invention is incorporating an additional use for ground coffee waste, extracting the oil it contains (typically 10-15%) to be used as a raw material to produce imidazolines with a high degree of unsaturation. The imidazoline mixtures obtained from the processes described in this invention are applicable, especially, as high-performance corrosion inhibitors, with low toxicity and good biodegradability.

Linoleic acid is the most abundant fatty acid in coffee oil and it is doubly unsaturated, conferring the imidazolines containing the hydrocarbonated chains of linoleic acid a superior adherence to metallic surfaces, even better than the adherence to metallic surfaces of imidazolines of other fatty acids, due to the interaction of the pi electrons of the double bonds with the electrons of the metallic surface.

The extraction method proposed for coffee oil improves on what has been described in literature, because it is a biphasic extraction that does not require coffee to be previously dried, including subsequent energy savings inherent to the evaporation of 550 to 650 kg of water per ton of coffee residue.

Coffee oil is submitted to a catalyzed transesterification process with KOH, employing the conventional methods described for the preparation of biodiesel, then, the biodiesel obtained is submitted to an aminolysis process with aminoethylethanolamine (AEEA), at between 140 and 160° C. and a subsequent heating process at a reduced pressure of 200 to 300 mmHg at the same temperature, until the stoichiometric amount of water is eliminated, to produce a mixture of imidazolines through cyclization of the intermediary amides produced during the aminolysis.

An alternative strategy that shortens the process is the direct treatment of the oil obtained from coffee waste, under the same conditions described above for biodiesel. With this alternative, the imidazolines produced contain the glycerol generated during the aminolysis process. The glycerol present in imidazoline mixtures of corrosion inhibitor formulas, does not affect the performance of the product.

Coffee waste is a well-known soil and water bank pollutant due to the toxic characteristics of caffeine. Utilizing the process described in this patent, the degreased residue improves the qualities of coffee as a fertilizer and as a raw material for compost, given that the biphasic process used to extract oil, completely eliminates any residual caffeine.

DETAILED DESCRIPTION

This invention describes two processes related to the preparation of imidazoline mixtures processing the oil obtained from ground coffee waste.

The structure of the main imidazolines of general formula (I) obtained from coffee oil is presented below:

Where position 1 of the imidazoline ring presents a 2-hydroxyethyl chain; and in position 2 (R), a hydrocarbonated chain of the following fatty acids present in oil obtained from coffee waste, mainly linoleic acid (Between 44 and 46%, preferably 44%) CH2(CH2)6CH=CHCH2CH=CH(CH2)4CH3; palmitic acid (between 32 to 35%, preferably 34%) —CH2(CH2)13CH3; and other minority fatty acids, among which oleic acid (Between 9 and 10%, preferably 9%, CH2(CH2)6CH=CH(CH2)7CH3; and stearic acid (between 6 and 7%, preferably 7%), —CH2(CH2)15CH3 can be found.

The main advantage of the imidazolines derived from linoleic acid is the presence of two double bonds on the hydrocarbonated chain, which confer the property of better adherence to metallic surfaces and consequently better performance as a corrosion inhibitor. This is due to the better stabilization capacity of the oxide layer and the longer duration of the hydrophobic effect, which minimizes contact of humidity with the metallic surface.

This invention includes two alternative processes to obtain the imidazoline mixtures derived from oil extracted from coffee waste. The first of these procedures, which we named process A, has three stages:

Stage 1. The extraction of the oil present in coffee waste, without previous drying, on a biphasic water-methanol-heptane system for batch processes or a water-heptane system for continuous processes, with the corresponding separation of the heptane layer and concentration until reaching dry state at moderately reduced pressure between 100 and 200 mmHg, retrieving heptane for reuse through a simple distillation method leaving oil totally free of volatile components, such as water or solvents.

Stage 2. The transesterification with methanol of the extracted coffee oil, catalyzed by KOH, to obtain biodiesel, with the subsequent separation of glycerol through a decantation process in a low ball tank with a see-through glass.

Stage 3. The final stage consists of two consecutive reactions: the aminolysis of biodiesel with aminoethylethanolamine (AEEA), at temperatures ranging between 140-160° C. and then the cyclization, by heating the sample at the same temperature, at pressures of 200-300 mmHg.

The second process for production of imidazolines from coffee waste contemplated by this invention, which we have named Process B, has two stages:

Stage 1. The extraction of the oil present in coffee waste, without previous drying, on a biphasic water-methanol-heptane system for batch processes or a water-heptane system for continuous processes, with the corresponding separation of the heptane layer and distillation at moderately reduced pressure between 100 and 200 mmHg, retrieving heptane for reuse through a simple distillation method, leaving oil totally free of volatile components, such as water or solvents.

Stage 2. Direct aminolysis of the oil extracted from waste coffee grounds with AEEA at temperatures ranging between 140-160° C. and then cyclization by heating the mixture at the same temperature, at pressures between 200-300 mmHg.

The imidazoline mixture mixture obtained according to process A is characterized by being glycerol free and the imidazoline mixture obtained according to process B is characterized by containing natural glycerol as a byproduct of the triglycerides of the oil. The imidazoline mixture obtained using any of the two alternative processes, presents high-performance properties as a corrosion inhibitor, including low toxicity and good biodegradability.

EXAMPLES

The examples presented below show the stages to produce the imidazoline mixtures for processes A and B respectively, as described in this invention's specifications.

Process A.

Stage 1

Coffee Waste Extraction

There was loaded 1 Kg of waste coffee with 60% humidity in a 5 L three-neck flask, 1 L of methanol and 1.4 L of heptane was added, and the mixture was heated until reflux with mechanic stirring at 489 RPM for 2 hours. It was cooled down to 35-40° C. and then filtered, the layers were separated and the methanol layer returned to the flask along with the solids. The heptane layer was concentrated under vacuum until dry. There was obtained 50.53 g of oil and 900 mL of heptane. The filter cake was loaded into the original flask, 1 L of heptane was added, and the mixture was heated at reflux for one additional hour, then cooled down to 25° C., filtered and the layers separated. The heptane layer was concentrated to dryness, obtaining 8.63 additional grams of oil. The oil obtained was submitted to obtain coffee biodiesel.

Stage 2
Coffee Biodiesel.

12.3 g of coffee oil was heated at 50° C. for 10 minutes, then a solution of 0.65 M of KOH/MeOH (184 mg in 5 mL) and was heated in an oil bath up to 80° C. for one hour. The complete transformation was verified by TLC (heptane-MTBE 9:1; iodine reagent). It was then cooled down to 25° C. and 130 µL, of AcOH was added, verifying pH=7. There was added 4 mL of MTBE and 6 mL of brine, stirred, and the layers were separated. The organic layer was dried over sodium sulfate and concentrated to retrieve 10.2 g of coffee biodiesel which was later processed to produce glycerol free imidazoline mixtures.

Stage 3
Preparation of Glycerol Free Imidazolines.

10 g of coffee biodiesel was loaded into a 25 mL flask and 3.42 g of aminoethylethanolamine were added. The mixture was then heated in oil up to 140° C. with a vacuum of 43 Kpa (322.5 mmHg) for four hours and then one hour at 16-20 mmHg. Transformation was verified by TLC (heptane-MTBE 9:1), (dichloromethane-MeOH—NH4OH 7:3+100 µL/mL). 12.12 g of raw imidazoline mixture was obtained.

Process B.
Stage 1
Coffee Waste Extraction.

There was loaded 1 Kg of waste coffee with 60% humidity in a 5 L three-neck flask, 1 L of methanol and 1.4 L of heptane was added, and the mixture was heated until reflux with mechanic stirring at 489 RPM for 2 hours. It was cooled down to 35-40° C. and then filtered, the layers were separated and the methanol layer returned to the flask along with the solids. The heptane layer was concentrated under vacuum until dry. There was obtained 50.53 g of oil and 900 mL of heptane. The filter cake was loaded into the original flask, 1 L of heptane was added, and the mixture was heated at reflux for one additional hour, then cooled down to 25° C., filtered and the layers separated. The heptane layer was concentrated to dryness, obtaining 8.63 additional grams of oil. The oil obtained was submitted to obtain coffee biodiesel.

Stage 2.
Direct Preparation of Imidazolines with Glycerol.

A 25 mL flask was loaded with 5 g of coffee oil and 1.636 g of AEEA and heated between 140-145° C. for one hour at atmospheric pressure and four hours at a reduced pressure of 322 mmHg. The complete disappearance of the triglycerides present in the oil was verified using TLC (heptane-MTBE 85:15) and (DCM-MeOH 7:3+100 µL/mL of NH4OH). There was obtained 5.3 g of a semisolid brownish mass. The imidazoline mixtures obtained using this process are characterized by containing natural glycerol.

Pilot Plant Scale Up

In a 100 gallon glass reactor (R-1), 52.5 kg of wet waste coffee grounds (63.14% humidity) was loaded, along with 66.33 Kg of methanol and 107.45 Kg of heptane. The mixture was heated to reflux with 120 RPM stirring for two hours and it was then cooled down to 35-40° C. It was then filtered in a Nutsche filter and the biphasic filtrate was transferred into a separating tank (T-1) to decant the lower methanol-water layer into the R-1 reactor, along with the filtered ground cake. The upper layer of T-1, which contained the heptanic oil extract, was transferred into a 100 gallon stainless steel reactor (R-2). The contents of R-1 were stirred and refluxed with 107.45 kg of heptane for two hours, then cooled down to 35-40° C. It was again filtered through a Nutsche filter, transferring the filtrate into a separating Tank (T-1). The aqueous-methanolic layer was transferred into a 50 gallon reactor to recover methanol; the residue was then sent to the treatment plant to be disposed. The upper layer was mixed in R-2 with the first extract. It was then concentrated at a reduced pressure of 200 mmHg down to a volume of 50-55 L and the residue was then concentrated to dryness in a 50 L rotavapor, yielding 3.93 kg of coffee oil (20.3% dry base).

Corrosion Inhibition Tests

Figure 1:
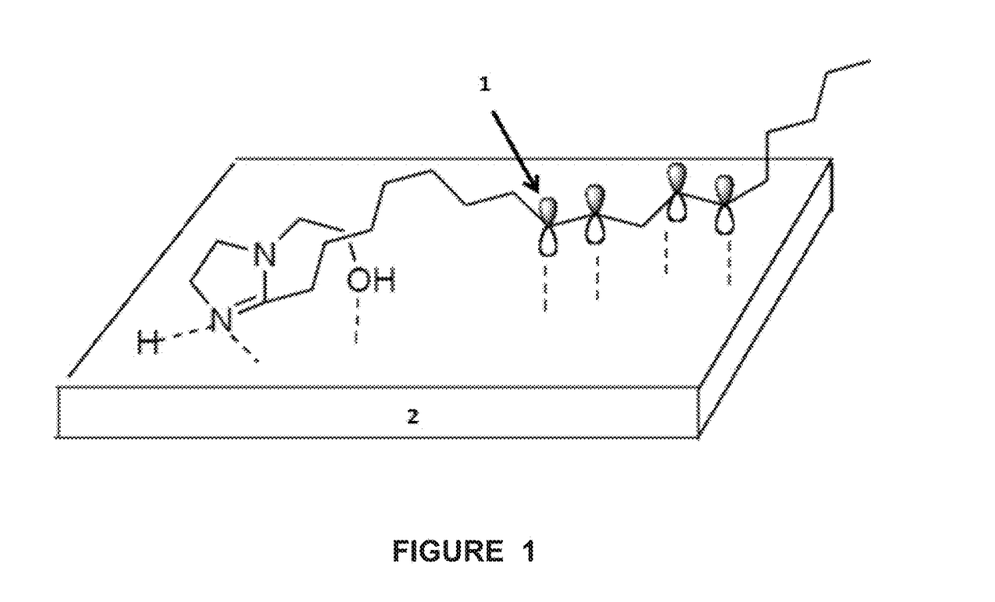
FIG. 1. Representation of the chemical structure of polyunsaturated imidazoline and its interactions with the metallic surface. The nitrogen and OH locations are marked. The foreseeable interactions with the metallic surface are marked in dotted lines, including the electronic clouds of such interactions.
Figure 2:
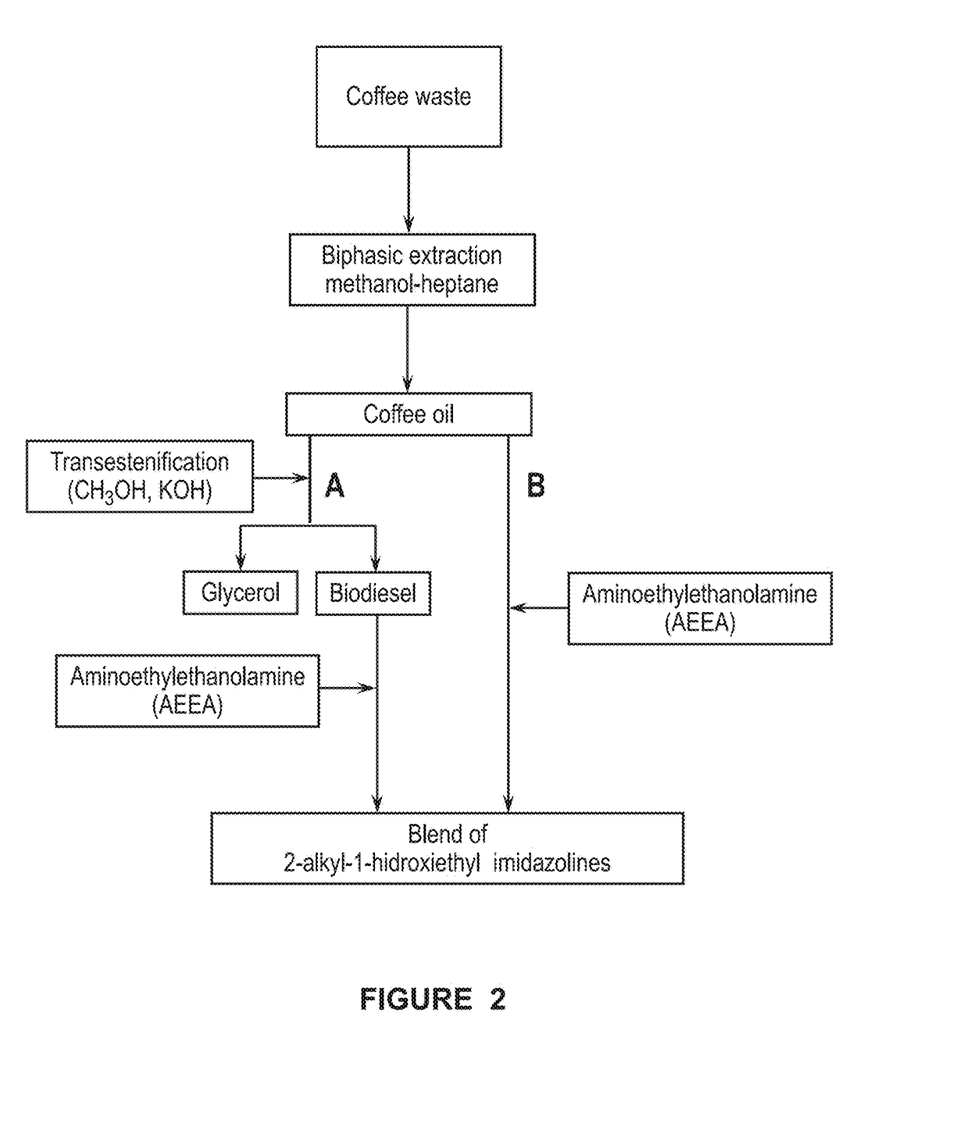
FIG. 2. Flowchart of the process to extract and transform waste coffee oil into imidazolines. Includes process A with three stages and process B with two stages.
Figure 3:
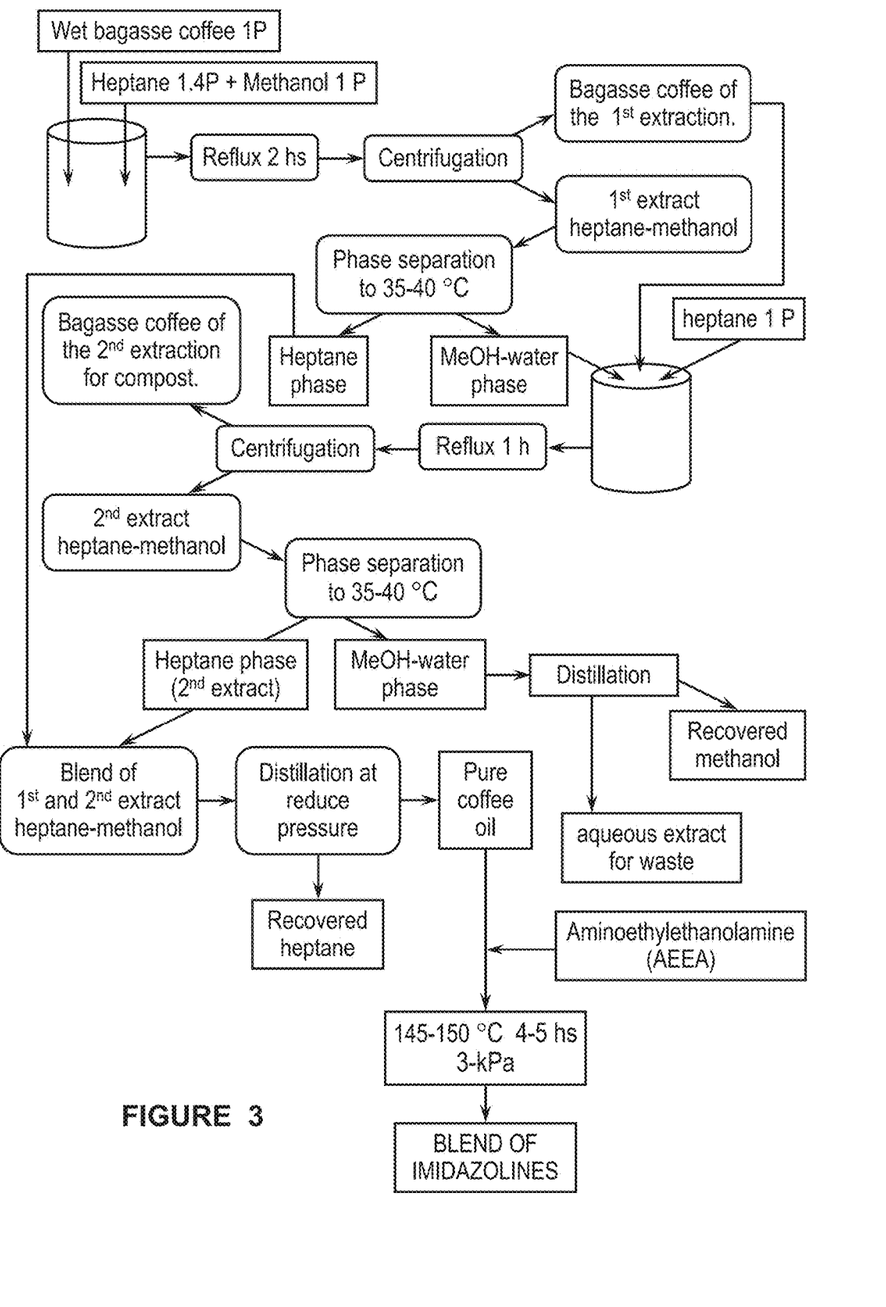
FIG. 3. Diagram of the process to obtain mixtures of imidazolines from coffee oil.
Figure 4A:
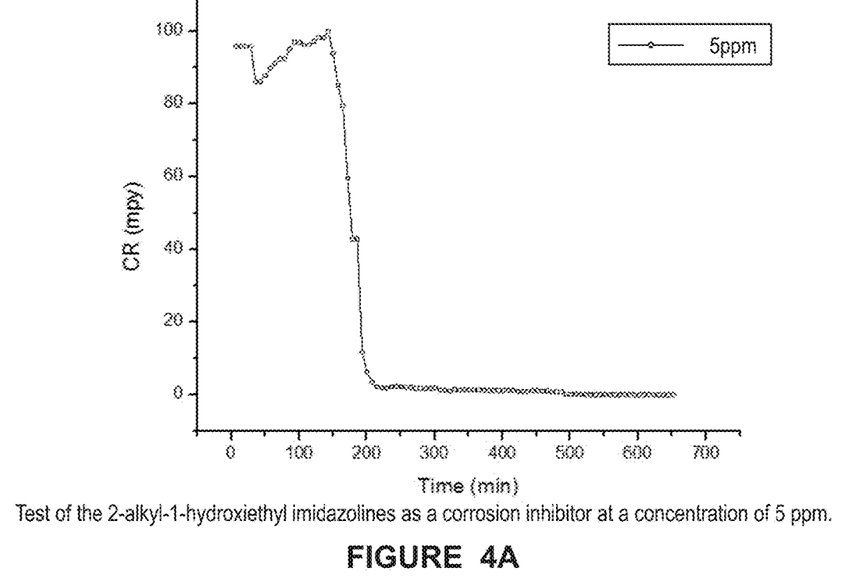
FIG. 4A. Test of the 1-hydroxyethyl-2-alkyl imidazolines as a corrosion inhibitor at a concentration of 5 ppm.
Figure 4B:
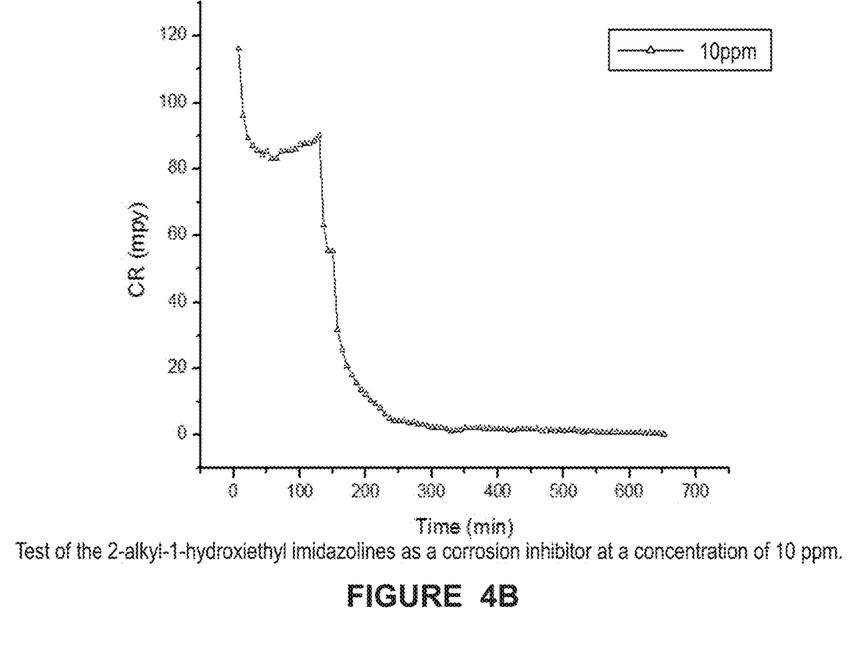
FIG. 4B. Test of the 1-hydroxyethyl-2-alkyl imidazolines as a corrosion inhibitor at a concentration of 10 ppm.
Figure 4C:
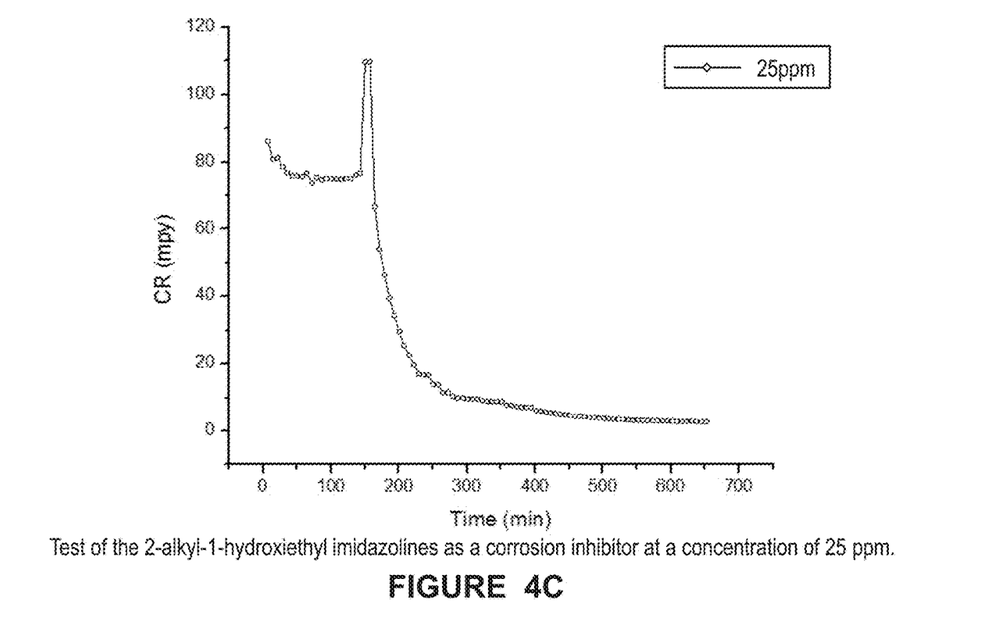
FIG. 4C. Test of the 1-hydroxyethyl-2-alkyl imidazolines as a corrosion inhibitor at a concentration of 25 ppm.
Figure 4D:
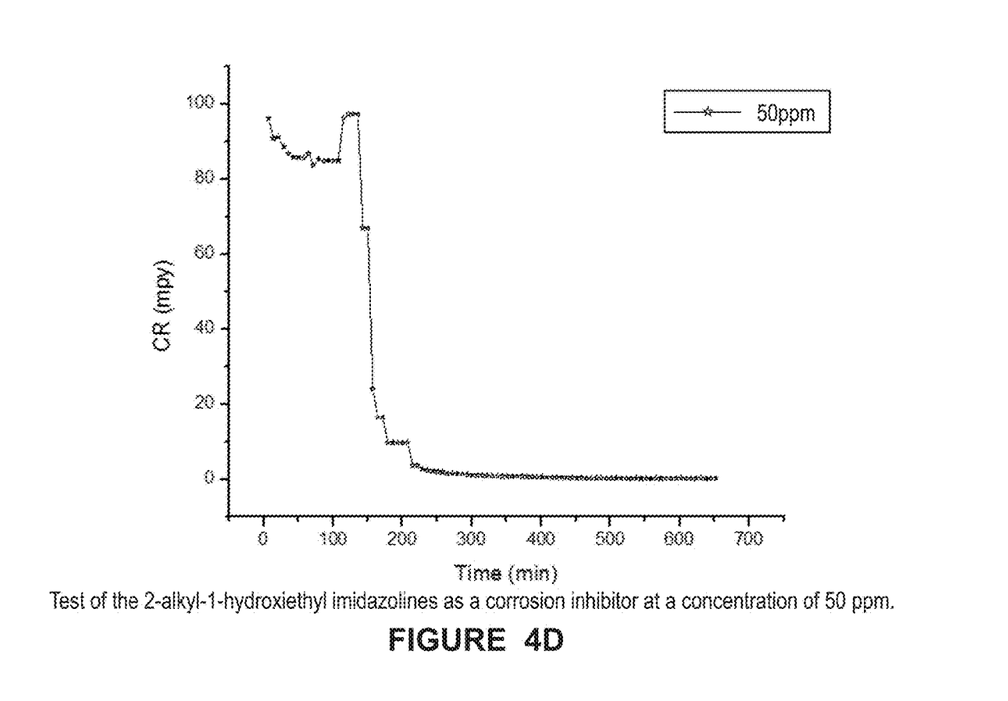
FIG. 4D. Test of the 1-hydroxyethyl-2-alkyl imidazolines as a corrosion inhibitor at a concentration of 50 ppm.
Figure 4E:
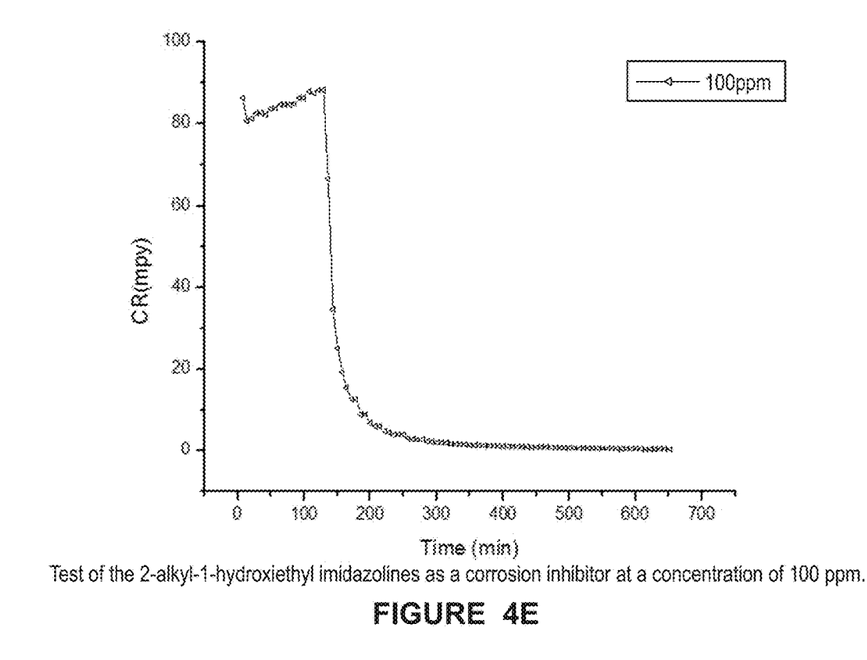
FIG. 4E. Test of the 1-hydroxyethyl-2-alkyl imidazolines as a corrosion inhibitor at a concentration of 100 ppm.

The effectiveness of the coffee residue imidazoline mixture produced using the procedures mentioned above was demonstrated conducting harmonic analysis and polarization resistance electrochemical corrosion tests. The corrosion tests were made on AISI 1018 type steel immersed in corrosive electrolytes at 3% NaCl, CO2 and H2S at saturation. FIGS. 4A, 4B, 4C, 4D and 4E, show the charts for the concentrations of the Imidazoline mixture at five, 10, 25, 50 and 100 ppm dissolved in the electrolytes mentioned above, and where the Y axis shows corrosion rate and the X axis shows time in minutes. The imidazoline mixture obtained showed effectiveness to mitigate corrosion below 0.05 mils of an inch per year at the concentrations mentioned.

What is claimed is:

1. A process for producing imidazoline mixtures, by processing oil extracted from waste coffee grounds, characterized by the following general formula in the mixture of Imidazolines (I), where the R represents the hydrocarbonated chain of one of the following fatty acids contained in coffee oil: linoleic acid in higher proportion, palmitic acid, oleic acid and stearic acid, wherein the process comprises the following stages:
a) extraction of ground coffee waste through a biphasic water-methanol-heptane or water-heptane extraction procedure, with the corresponding separation of the heptanic layer and the concentration to dryness under moderately reduced pressure between 100 and 200 mmHg, retrieving heptane to be reused and leaving the oil completely free of volatile components, a majority of the methanol used is recovered through the distillation of the aqueous layer,
b) coffee oil is submitted to a transesterification process catalyzed with KOH, obtaining coffee biodiesel and glycerol, with the glycerol then being separated from the mixture through a decantation process in a tank; and
c) the coffee biodiesel obtained is submitted to aminolysis procedure with aminoethylethanolamine (AEEA), heating to between 140 and 160° C. and a later heat cyclation process at the same temperature and 200 to 300 mmHg until removal of the stoichiometric amount of water, to produce a mixture of imidazolines of general formula (I).

2. A process for producing imidazoline mixtures processing the oil extracted from ground coffee waste, wherein that the imidazoline mixture obtained presents the following general formula (I), where R represents the hydrocarbonated chain of one of the following fatty acids contained in coffee oil: linoleic acid in greater proportion, palmitic acid, oleic acid and stearic acid, wherein the process comprises the following stages:
a) extraction of ground coffee waste, through a biphasic water-methanol-heptane or water-heptane extraction procedure, with the corresponding separation of the heptanic layer and the concentration until dryness and moderately reduced pressure between 100 and 200 mmHg retrieving heptane to be reused and leaving the oil completely free of volatile components; the larger amount of methanol is retrieved through the distillation of the aqueous layer; and
b) the coffee oil obtained is submitted to an aminolysis procedure with aminoethylethanolamine (AEEA), heating to between 140 and 160° C. and a later heat cycling process at the same temperature and 200 to 300 mmHg until eliminating the stoichiometric amount of water, to produce a mixture of imidazolines of general formula (I).

* * * * *